United States Patent
Gandemo

(10) Patent No.: US 7,351,236 B2
(45) Date of Patent: Apr. 1, 2008

(54) ABSORBENT ARTICLE WITH IMPROVED CLOSING MECHANISM

(75) Inventor: Tomas Gandemo, Askim (SE)

(73) Assignee: SCA Hygiene Products, AB, Gothenburg (SE)

( * ) Notice: Subject to any disclaimer, the term of this patent is extended or adjusted under 35 U.S.C. 154(b) by 307 days.

(21) Appl. No.: 10/717,541

(22) Filed: Nov. 21, 2003

(65) Prior Publication Data

US 2005/0113792 A1    May 26, 2005

(51) Int. Cl.
*A61F 13/15* (2006.01)
(52) U.S. Cl. .............. 604/389; 604/387; 604/385.03; 604/391; 604/394; 604/396
(58) Field of Classification Search ........... 604/385.03, 604/387, 389, 391, 394, 396
See application file for complete search history.

(56) References Cited

U.S. PATENT DOCUMENTS

| | | | |
|---|---|---|---|
| 4,205,679 A | 6/1980 | Repke et al. | |
| 5,370,634 A | 12/1994 | Ando et al. | |
| 6,120,489 A | 9/2000 | Johnson et al. | |
| 6,264,641 B1 | 7/2001 | Van Gompel et al. | |

2002/0112276 A1    8/2002    Ruman et al.

FOREIGN PATENT DOCUMENTS

| | | |
|---|---|---|
| GB | 2267024 A | 11/1993 |
| JP | 10-155834 | 6/1998 |
| WO | 89/07897 A1 | 9/1989 |
| WO | 96/35305 A1 | 11/1996 |
| WO | 98/18421 A1 | 7/1998 |

*Primary Examiner*—Jacqueline F. Stephens
(74) *Attorney, Agent, or Firm*—Buchanan, Ingersoll & Rooney PC

(57) ABSTRACT

The invention relates to an absorbent article (100) such as a diaper or an incontinence protector, which absorbent article is designed like underpants, with a first leg opening (120) and a second leg opening (130) and a waist opening (110), where the article comprises at least a first openable seal line (140) arranged at the first leg opening, and first (150', 170') and second (150, 170) opening and closing means arranged to be able to cooperate with one another when the openable seal line (140) is broken. The first (150', 170') and second (150, 170) closing means are situated on respective sides of the seal line (140) and are arranged on the surface of the underpants (100), the first closing means (150', 170') being arranged on the inside of the underpants and the second closing means (150, 170) being arranged on the outside of the underpants. The first (150', 170') and second (150, 170) opening and closing means are expediently arranged substantially parallel to the main line of extent of the seal line (140).

8 Claims, 2 Drawing Sheets

ABSORBENT ARTICLE WITH IMPROVED CLOSING MECHANISM

TECHNICAL FIELD

The present invention relates to an absorbent article such as a diaper or an incontinence protector designed like underpants. The absorbent article comprises at least a first openable seal line and first and second opening and closing means which are arranged to be able to cooperate with one another when the openable seal line is broken.

BACKGROUND ART

Absorbent articles designed like underpants, so called diaper pants, have been known for some time. As the name indicates, these articles are designed like shorts or briefs. To make things easier for the user, the articles are often pre-configured like underpants when supplied.

To make things easier for the user or for nursing staff, parents or the like, the diaper pants are often made up like underpants with the aid of an openable seal line, for example a thermal weld seam, which is expediently arranged at one leg opening of the underpants and extends from the waist line of the underpants down to the leg opening.

With the aid of the openable seal line, the diaper pants can be opened in order to check whether they have to be changed, for example. If it is found that the diaper pants do not have to be changed, it is necessary to be able to close the diaper again. If the seal line is a thermal weld seam or some other type of closure which cannot be re-closed, the diaper pants in other words have to be provided with means for re-closing them after the seal line has been opened. These means for re-closing the diaper pants are expediently of a type which can be used over again, i.e. permits repeated opening and re-closing in order to check the state of the diaper pants.

Known solutions to this problem are disclosed in, for example, documents GB 2 267 024 and U.S. Pat. No. 5,370,634. Both of these documents disclose diaper pants with seal lines of the once-only type, where the diaper pants are provided with two-part re-closing means of a type which can be used more than once, for example touch-and-close tapes.

According to the prior art disclosed in, for example, the two abovementioned documents, one part of the two-part means for re-closing is arranged on separate flaps which protrude from the natural shape of the underpants, beyond the original seal line, and the second part is arranged on the underpants as a "target area" for the flap.

The prior art thus has a number of disadvantages: the separate flaps which are used make manufacture of the diaper pants more difficult and thus make production more expensive. In addition, the speed of production is reduced by the diaper pants having to be provided with separate flaps.

Moreover, the use of flaps entails increased material consumption in the manufacture of the diaper pants, which makes the product more costly to produce.

DISCLOSURE OF THE INVENTION

There is therefore a need for an absorbent article which can already be in the shape of diaper pants when supplied to the customer, and at the same time the diaper pants in question must be able to be opened and re-closed more easily than in the prior art, and the diaper pants must have a lower production cost than in the prior art.

This need is satisfied by the present invention which discloses an absorbent article such as a diaper or an incontinence protector, which absorbent article is designed like underpants, with a first leg opening and a second leg opening and with a waist opening. The article comprises at least a first openable seal line arranged at the first leg opening, and first and second opening and closing means arranged to be able to cooperate with one another when the openable seal line is broken. The first and second closing means are situated on respective sides of the seal line and are arranged on the surface of the underpants, the first closing means being arranged on the inside of the underpants, and the second closing means being arranged on the outside of the underpants.

The first and second closing means are expediently arranged substantially parallel to the main line of extent of the seal line.

This design of an absorbent article according to the invention makes it possible to produce diaper pants which, when supplied to the customer, can be closed along an openable seal line of the once-only type, for example with the aid of a thermal weld seam. On first checking the state of the diaper pants, this seal line is torn open and, if it is necessary to re-close the diaper pants, this is done with the aid of the first and second closing means, which are simply brought toward one another. In a preferred embodiment, the opening and closing means are arranged so that closing can be done by means of the opened edges quite simply being made to overlap and being pressed against one another.

Thus, by means of the invention, it has become possible to eliminate the need for separate flaps while still obtaining re-closable diaper pants which are less expensive and easier to produce than known diaper pants. Further advantages of the present invention will become apparent from the following detailed description.

DESCRIPTION OF THE FIGURES

The invention will be described below in more detail with reference to the attached drawings, in which.

EMBODIMENTS

Figure 1:
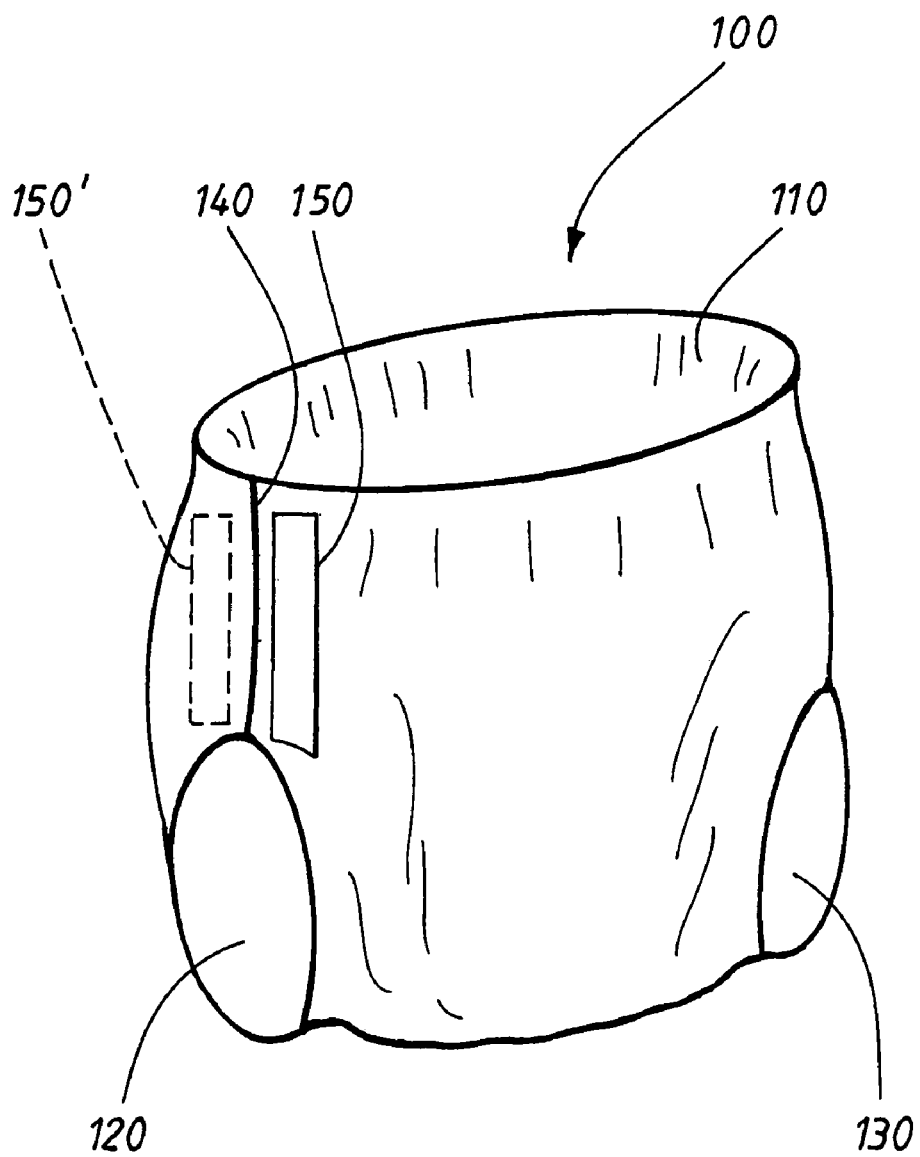
FIG. 1 shows an example of an absorbent article according to the invention.

FIG. 1 shows an absorbent article according to the invention, namely diaper pants 100, in the state in which the article has been made ready for delivery.

The diaper pants 100 thus comprise a waist opening 110, and a first leg opening 120 and second leg opening 130. At at least one leg opening 120, the diaper pants 100 are closed with the aid of an openable seal line 140 which is produced, for example, with the aid of thermal welding, ultrasonic welding or the like.

When the status of the diaper pants is to be checked for the first time by opening them, the openable seal line 140 is torn open. If it is found that the diaper pants can continue to be used, or for some other reason are not to be removed, it is therefore necessary to be able to close them again at the line defined by the openable seal line 140.

According to the invention, the diaper pants 100 are provided with first 150 and second 150' opening and closing means which are arranged to be able to cooperate with one another when the openable seal line 140 has been broken.

According to the invention, the first 150 and second 150' opening/closing means are situated on respective sides of the seal line 140 and are arranged on the surface of the diaper pants, in such a way that the first opening/closing means 150 is arranged on the inside of the underpants and the second opening/closing means 150' is arranged on the outside of the diaper pants.

It is expedient, but not essential, that the first 150 and second 150' opening/closing means are arranged in immediate proximity to the seal line 140 and expediently run along in principle the same extent as the seal line, in other words most of the way from the waist opening 110 to the first leg opening 120. The opening/closing means therefore do not consist of tabs or flaps protruding from the rest of the diaper pants but instead lie directly on the outside/inside of the diaper pants.

It is also expedient if the first 150 and second 150' opening/closing means are arranged so that they run parallel to the seal line 140.

When the seal line 140 has been broken, it is necessary in other words to re-close the diaper pants 100 along essentially the same line by placing the opened edges overlapping so that the first opening/closing means 150 comes into engagement with the second opening/closing means 150'. Thereafter, it is possible, in principle, to open and close them any number of times with the aid of these opening/closing means.

The opening and closing means can of course be of a large number of different types without this affecting the invention. Examples which may be mentioned, however, are the "hook and loop" type, different types of adhesive surfaces, or surfaces interacting in some other way, and, for example, press buttons. In this connection, the material of all or part of one surface of the diaper pants, expediently the surface facing away from the user, can constitute one of these interacting surfaces, for example the loops in a "hook and loop" system.

Figure 2:
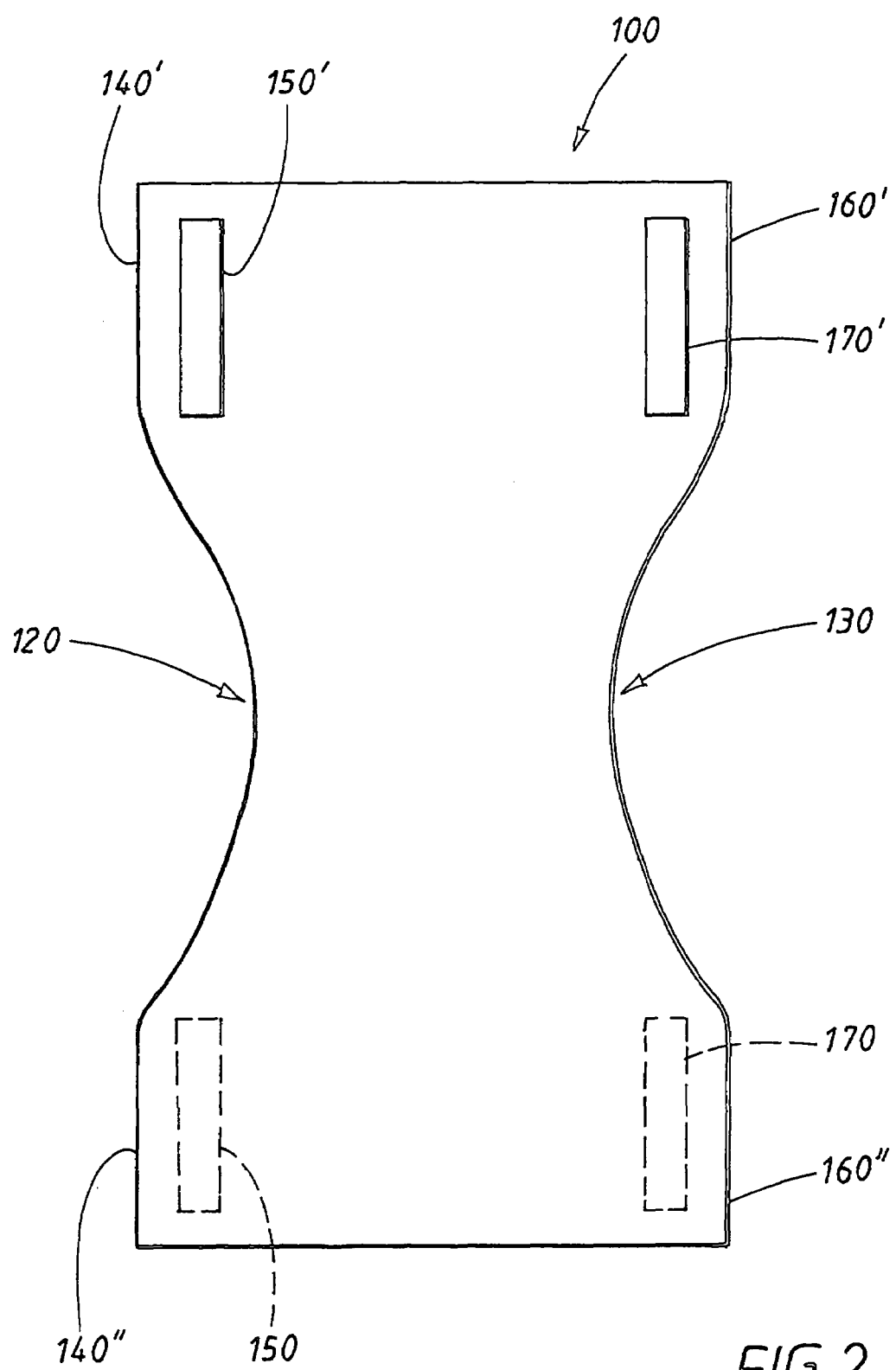
FIG. 2 shows the article from FIG. 1 in an opened state.

In FIG. 2, the diaper pants 100 from FIG. 1 are shown in the opened state. It will be seen from FIG. 2 that the diaper pants are expediently provided with second opening/closing means 170, 170' at the other leg opening 130. The second opening/closing means 170, 170' expediently correspond largely to the first opening/closing means 150, 150' as regards position and configuration, for which reason the second opening/closing means 170, 170' will not be described in detail here.

In FIG. 2, the same reference numbers have been used as in FIG. 1 for corresponding parts of the diaper pants 100, except for the fact that the two edges forming the seal line 140 have been designated by 140' and 140", and corresponding edges forming a second seal line at the second leg opening have been designated by 160' and 160".

The invention is not limited to the illustrative embodiments described above and instead can be freely varied within the scope of the appended patent claims. For example, the opening/closing means do not have to run parallel to the seal lines and instead they can be arranged in numerous different ways in which they can come into engagement with one another.

The invention claimed is:

1. An absorbent article designed like underpants, with a pants chassis, a first leg opening, a second leg opening and a waist opening, the absorbent article comprising:

at least a first openable seal line arranged at the first leg opening, said first openable seal line having a first sealed configuration defined by said first openable seal line being sealed by a predetermined sealing means prior to use and, after the predetermined sealing means is broken, a second resealable configuration; and first and second opening and closing means arranged to cooperate with one another when the predetermined sealing means of the openable seal line is broken so as to releasably reseal the openable seal line in the second resealable configuration, wherein the first and second opening and closing means are situated on respective sides of the first openable seal line and are arranged entirely on a surface of the pants chassis, the first opening and closing means being arranged entirely on an inside surface of the pants chassis and the second opening and closing means being arranged entirely on an outside surface of the pants chassis such that a first opened edge of the openable seal line is overlapped with a second opened edge of the openable seal line when the openable seal line is resealed in the second resealable configuration.

2. The absorbent article as claimed in claim 1, wherein the first and second opening and closing means are arranged substantially parallel to a main line of extent of the first openable seal line.

3. The absorbent article as claimed in claim 1, wherein the first and second opening and closing means comprise touch-and-close tapes.

4. The absorbent article as claimed in claim 1, wherein the first and second opening and closing means comprise adhesive surfaces.

5. The absorbent article as claimed in claim 1, wherein the first openable seal line arranged at the first leg opening defines a substantially linear line.

6. The absorbent article as claimed in claim 1, further comprising a second openable seal line arranged at the second leg opening.

7. The absorbent article as claimed in claim 1, wherein in the first sealed configuration of the openable seal line, said absorbent article defines a pants diaper shape, and said first and second opening and closing means are disposed so as not to protrude beyond the pants diaper shape.

8. The absorbent article as claimed in claim 1, wherein in both the first sealed configuration and the second resealable configuration of the openable seal line, said first and second opening and closing means are disposed so as not to protrude beyond the openable seal line.

* * * * *